(12) United States Patent
Chowdhury

(10) Patent No.: US 11,278,678 B2
(45) Date of Patent: Mar. 22, 2022

(54) IN OR RELATED TO TRANSDERMAL DELIVERY

(71) Applicant: NDM TECHNOLOGIES LIMITED, Loughborough (GB)

(72) Inventor: Dewan Fazlul Hoque Chowdhury, Loughborough (GB)

(73) Assignee: NDM Technologies Limited, Loughborough (GB)

( * ) Notice: Subject to any disclaimer, the term of this patent is extended or adjusted under 35 U.S.C. 154(b) by 524 days.

(21) Appl. No.: 16/305,877

(22) PCT Filed: May 30, 2017

(86) PCT No.: PCT/GB2017/051540
§ 371 (c)(1),
(2) Date: Nov. 29, 2018

(87) PCT Pub. No.: WO2017/207980
PCT Pub. Date: Dec. 7, 2017

(65) Prior Publication Data
US 2019/0125984 A1 May 2, 2019

(30) Foreign Application Priority Data
May 31, 2016 (GB) ..................................... 1609518

(51) Int. Cl.
*A61M 5/46* (2006.01)
*A61M 5/315* (2006.01)
(Continued)

(52) U.S. Cl.
CPC ................ *A61M 5/46* (2013.01); *A61M 5/20* (2013.01); *A61M 5/31515* (2013.01);
(Continued)

(58) Field of Classification Search
CPC .......... A61M 5/3287; A61M 2005/206; A61M 2005/14252; A61M 2005/14284; A61M 2005/1585
See application file for complete search history.

(56) References Cited

U.S. PATENT DOCUMENTS

| 1,688,332 A | 10/1928 | Heck, Jr. et al. |
| 3,675,766 A | 7/1972 | Rosenthal |

(Continued)

FOREIGN PATENT DOCUMENTS

| CN | 2013/99158 | 2/2010 |
| DE | 23 19 591 A1 | 11/1974 |

(Continued)

OTHER PUBLICATIONS

International Search Report and Written Opinion, PCT/GB2017/051540, NDM Technologies Lmited, 12 pages (dated Sep. 22, 2017).

(Continued)

*Primary Examiner* — Nathan R Price
*Assistant Examiner* — Courtney B Fredrickson
(74) *Attorney, Agent, or Firm* — Foley & Lardner LLP

(57) ABSTRACT

A needle delivery device (10) comprises a needle assembly (4, 5), a drive mechanism (2, 3) and a contact member (6). The drive mechanism (2, 3) includes a drive member (2) which is linearly moveable upon rotation of the drive member (2). The contact member (6) is positioned between and abutting the needle assembly (4, 5) and the drive member (2). The contact member (6) is configured to provide only linear motion to the needle assembly (4, 5) upon rotation of the drive member (2) so as to drive movement of the needle assembly (4, 5) between a distal and proximal direction relative to the needle delivery device (10).

20 Claims, 9 Drawing Sheets

(51) Int. Cl.
  *A61M 5/42*   (2006.01)
  *A61M 5/32*   (2006.01)
  *A61M 5/20*   (2006.01)
  *A61M 5/142*   (2006.01)
  *A61M 5/158*   (2006.01)

(52) U.S. Cl.
  CPC ............ *A61M 5/3287* (2013.01); *A61M 5/42* (2013.01); *A61M 2005/14252* (2013.01); *A61M 2005/1585* (2013.01); *A61M 2005/206* (2013.01); *A61M 2005/31518* (2013.01); *A61M 2005/3289* (2013.01); *A61M 2205/13* (2013.01); *A61M 2205/50* (2013.01)

(56) References Cited

U.S. PATENT DOCUMENTS

| | | | |
|---|---|---|---|
| 3,918,449 | A | 11/1975 | Pistor |
| 5,139,029 | A | 8/1992 | Fishman et al. |
| 5,496,304 | A | 3/1996 | Chasan |
| 5,843,114 | A | 12/1998 | Jang |
| 5,865,794 | A | 2/1999 | Castro |
| 6,006,798 | A | 12/1999 | Lindquist |
| 6,280,414 | B1 | 8/2001 | Shah et al. |
| 6,589,202 | B1 | 7/2003 | Powell |
| 6,663,613 | B1 | 12/2003 | Evans et al. |
| 8,353,871 | B2 | 1/2013 | Zimmerman et al. |
| 2001/0007059 | A1 | 7/2001 | Mirzaee |
| 2002/0013615 | A1 | 1/2002 | Haim et al. |
| 2002/0087144 | A1 | 7/2002 | Zinger et al. |
| 2003/0040712 | A1 | 2/2003 | Ray et al. |
| 2003/0105430 | A1 | 6/2003 | Lavi et al. |
| 2003/0216693 | A1 | 11/2003 | Mickley |
| 2004/0087992 | A1 | 5/2004 | Gartstein et al. |
| 2005/0269226 | A1 | 12/2005 | Erickson et al. |
| 2006/0206062 | A1 | 9/2006 | Naimark et al. |
| 2007/0197968 | A1 | 8/2007 | Pongpairochana et al. |
| 2009/0093792 | A1 | 4/2009 | Gross et al. |
| 2009/0234288 | A1 | 9/2009 | Fischer |
| 2009/0312691 | A1 | 12/2009 | Kim et al. |
| 2013/0317431 | A1 | 11/2013 | Kramer et al. |
| 2014/0142507 | A1 | 5/2014 | Armes |
| 2016/0193405 | A1 | 7/2016 | Schabbach et al. |
| 2018/0353708 | A1* | 12/2018 | Schader ............... A61M 5/20 |

FOREIGN PATENT DOCUMENTS

| | | |
|---|---|---|
| EP | 0 370 336 A2 | 5/1990 |
| EP | 1 598 043 A1 | 11/2005 |
| EP | 2 636 419 A1 | 9/2013 |
| EP | 2 674 179 A1 | 12/2013 |
| EP | 2 822 620 B1 | 4/2018 |
| GB | 2 254 787 A | 10/1992 |
| JP | H09-262294 A | 10/1997 |
| JP | 2000-014782 A | 1/2000 |
| JP | 2002-204817 A | 7/2002 |
| JP | 2009-291373 A | 12/2009 |
| KR | 200395359 | 9/2005 |
| WO | WO-88/06133 A1 | 8/1988 |
| WO | WO-90/11789 | 10/1990 |
| WO | WO-96/35466 | 11/1996 |
| WO | WO-97/21457 | 6/1997 |
| WO | WO-2004/045671 A2 | 6/2004 |
| WO | WO 2005/072795 A2 | 8/2005 |
| WO | WO-2005/074860 A1 | 8/2005 |
| WO | WO 2008/024810 A2 | 2/2008 |
| WO | WO-2012/035334 A1 | 3/2012 |
| WO | WO-2012/169993 A1 | 12/2012 |
| WO | WO-2013/134246 | 9/2013 |
| WO | WO-2015/032747 A1 | 3/2015 |
| WO | WO-2015/036616 A1 | 3/2015 |
| WO | WO-2015/048791 A1 | 4/2015 |
| WO | WO-2015/091760 | 6/2015 |
| WO | WO-2015/118358 A1 | 8/2015 |

OTHER PUBLICATIONS

International Search Report and Written Opinion, PCT/GB2017/052043, dated Apr. 9, 2018, 16 pages.
International Search Report and Written Opinion, PCT/GB2017/052045, dated Nov. 7, 2017, 10 pages.
Office Action issued in United Kingdom Application No. 1612171.7 dated Oct. 28, 2021.
Sibuet, System for securing a needle on a syringe, Google Patents Translatoin (Year: 1989).

* cited by examiner

IN OR RELATED TO TRANSDERMAL DELIVERY

CROSS-REFERENCE TO RELATED APPLICATIONS

This application is a U.S. National Stage Application of PCT/GB2017/051540, filed May 30, 2017, which claims the benefit of and priority to Great Britain Patent Application No. 1609518.4, filed May 31, 2016, both of which are incorporated herein by reference in their entireties.

TECHNICAL FIELD

This invention relates to a needle delivery device, a plunger mechanism and a syringe.

BACKGROUND

It is known to deliver drugs through the skin, i.e. transdermally, by using a needle.

When needles are pushed into the skin for drug administration or diagnostics purposes, whether for animal or human applications, the use of large forces leads to trauma and tissue damage.

It is preferable to be able to use very low forces to breach the outer layer of the skin such that the trauma to the outer layer is minimal as this poses the toughest barrier to the insertion of any object into the skin. Once the outer barrier is breached the lower deeper layers of the skin are essentially soft tissue thus the forces required are not as high, but also the insertion speed could be increased if desired to deliver a dose very rapidly.

SUMMARY

According to an aspect of the invention there is provided a needle delivery device comprising:
a needle assembly;
a drive mechanism including a drive member, the drive member being linearly moveable upon rotation of the drive member; and
a contact member positioned between and abutting the needle assembly and the drive member, the contact member being configured to provide only linear motion to the needle assembly upon rotation of the drive member so as to drive movement of the needle assembly between a distal and proximal position relative to the needle delivery device.

Such an arrangement readily provides linear movement of the needle assembly so as to penetrate skin of a patient whilst minimising the trauma to the skin which would otherwise be caused by the needle assembly additionally rotating. Such additional rotation of the needle assembly would cause trauma to the skin because the needle part may not be concentric, nor may any solid dose attached to the needle, thus if the needle part was to rotate then this would lead to increased trauma of the skin.

In particular, this is because the drive member is not directly attached to the needle assembly which is being inserted into the skin. The drive member merely acts to exert pressure on the part of the device to which the needle is attached, i.e. the contact member, in order to insert the needle into the skin.

Moreover, rotating the drive member which is in direct contact with the contact member (and thus indirectly in contact with the needle assembly) reduces the number of components and overall footprint of the needle delivery device whilst being able to utilize a readily available actuator such as a motor (which typically provides rotational movement). In contrast, having the drive member only move in a linear manner would mean having another component that rotates, thus increasing the component count and overall footprint of the device.

Preferably, the surface of the contact member abutting the drive member provides a low friction which prevents translation of the rotational movement of the drive member to the contact member.

Optionally the low friction is provided by a low friction material. Such material may be a coating on the contact member or may instead be a piece of low friction material that is layered or adhered to the remainder of the contact member. Preferably, the low friction material is produced from metal, plastic, glass, Teflon, or another polymeric composition or glass composition, or a combination thereof.

Ideally, the coefficient of friction (CoF) between the drive member and the contact member is less than, or equal to, about 1.0, preferably less than or equal to 0.5, more preferably less than or equal to 0.2. The skilled person is aware of the methods used for calculating the CoF between objects.

Conveniently the drive member includes a threaded shaft and the drive mechanism further includes a fixed drive plate, wherein the threaded shaft and the fixed drive plate are threadably engaged with one another. As such, the drive mechanism is linearly moveable relative to the fixed drive plate upon rotation of the drive member.

The needle delivery device may further include a control assembly operatively coupled to the drive mechanism and being configured to provide a rotational drive to the drive mechanism at variable driving speeds.

Preferably the control assembly is configured to increase the driving speed once the needle assembly has penetrated the skin.

In this way, the force of the needle assembly on the skin is initially gradual and low until the skin is breached, after which the speed of insertion may increase rapidly if desired for rapid dose delivery. Such initial gradual and low force reduces the trauma to the skin.

Advantageously, the needle delivery device further comprises a sensor and the control assembly receives data from the sensor which is able to detect when the needle assembly has penetrated the skin.

Such a sensor may be a pressure transducer, or some other device capable of detecting the change in resistance during the needle insertion process. Alternatively it may be in the form of a measuring device which measures the needle position relative to the surface of the skin, indicating when the needle tip is in a position that is below the surface of the skin, once skin elasticity and rebound is taken into account.

In an embodiment of the invention, the control assembly is also operatively coupled to a plunger mechanism of the needle delivery device, the control assembly being further configured to activate the plunger mechanism so as to expel a pharmaceutical composition at a predetermined distance of linear movement of the drive member.

Such an arrangement permits delivery of a drug dose (pharmaceutical composition) at a predetermined depth of penetration of the needle assembly into the skin of a patient. Accordingly, accurate drug delivery can be achieved.

Preferably, the control assembly is further still configured to activate the plunger mechanism at a number of discrete predetermined distances of linear movement of the drive member so as to expel a desired volume of pharmaceutical composition at each discrete distance.

Such an arrangement permits delivery of discrete volumes of drug dose at different predetermined depths of penetration of the needle assembly into the skin of a patient without having to puncture the skin more than once.

Optionally, a first discrete predetermined distance is at a proximal position relative to the needle delivery device and the last discrete predetermined distance is at a distal position relative to the needle delivery device.

Having the first discrete predetermined distance at a proximal position and the last discrete predetermined distance at a distal position permits the aforementioned discrete volumes of drug dose to be delivered at different depths, starting at a shallow insertion point and gradually working deeper into the skin.

This is in contrast to some conventional injections where the operator/care provider would insert the needle deep into the skin, and then gradually withdraw the needle and inject further volumes at different heights. The problem with such a conventional method is that if the operator/care provider has drawn the needle too far out of the skin and there is a significant dose remaining then one must re-insert the needle which poses infection issues as well as pain and potential loss of dose.

Preferably, the control assembly provides the rotational drive to the drive member. The control assembly may instead provide the rotational drive to the fixed drive plate.

Advantageously, the control assembly includes a motor which provides the rotational drive.

Preferably, the control assembly includes an electronic controller which is pre-programmable. The electronic controller can then be pre-programmed to carry out any of the functions described hereinabove. For example, the delivery of a drug dose can be controlled to different depths of the skin by pre-programming the drive mechanism and synchronizing with the plunger mechanism, such that the drive mechanism drives the needle assembly into the skin at a first pre-determined depth, followed by insertion of some of the drug dose, followed by further insertion and so on.

In another example, the delivery of a solid drug dose can be controlled by a feedback mechanism, whereby very gradual force would be applied by the drive mechanism to the needle assembly, and a feedback loop would measure the resistive force (via the sensor mentioned above) as it increases. At a point where the skin is breached/punctured there would be a sudden drop in the resistance. At this point the electric controller may be pre-programmed to then alter the drive speed provided to the drive mechanism so as to alter the speed at which the needle is inserted into the skin (i.e. starting with a slow speed followed by a rapid insertion of the solid dose direction into the skin at a desired depth).

According to another aspect of the invention, there is provided a plunger mechanism for a drug injection device, including a plunger rod having first and second opposed ends and a flexible portion extending therebetween, the first end being abuttable in use to a stopper and the second end including a tractive portion, the plunger mechanism further including an actuator in contact with the tractive portion of the plunger rod, wherein movement of the actuator drives the plunger rod linearly along the length of the tractive portion.

The inclusion of a flexible portion of the plunger rod permits the first and second ends to be positioned obliquely away from another, instead of being in line with one another, so as to reduce the overall length of the plunger mechanism.

Conveniently, the tractive portion of the plunger rod is threaded.

Meanwhile, the tractive portion and actuator arrangement permits linear movement of the plunger rod which will, in use, move the stopper so as to dispense a pharmaceutical composition from a barrel or vial. Such an arrangement can be manually operated or can be fully automated, e.g. operated by a motor.

The actuator could be provided in many different forms, such as two wheels on either side of the tractive portion of the plunger rod, with the plunger rod being linearly moveable on rotation of the wheels. The actuator could engage and move the plunger rod with high friction, or may be provided with teeth or a threaded portion.

Preferably the first and second ends of the plunger rod align parallel with one another with the flexible portion being bent therebetween.

Such an arrangement makes full use of the flexible portion of the plunger rod so as to minimise the overall length of the plunger mechanism, thus providing a compact design from a user-perspective as well as a storage and distribution perspective.

In contrast, FIG. 4 shows a conventional plunger arrangement being used in a syringe. The plunger rod is in the extended position and when you take into account the full extended position and the outer housing of the syringe, the length of the device becomes cumbersome and more difficult to use.

Optionally, the actuator includes a threaded member positioned adjacent to and threadably engaged with the threaded portion of the plunger rod. Alternatively, the actuator may include a threaded nut surrounding the threaded portion of the plunger rod and a threaded member positioned adjacent to and threadably engaged with the threaded nut.

According to a further aspect of the invention there is provided a syringe including a needle delivery device and a plunger mechanism as described hereinabove. The needle delivery device and the plunger mechanism are preferably operatively coupled to one another According to a further still aspect of the invention there is provided a method of administrating a pharmaceutical composition to a patient using a syringe as described hereinabove.

BRIEF DESCRIPTION OF THE THE FIGURES

There now follows a brief description of preferred embodiments of the invention, by way of non-limiting examples, with reference being made to the accompanying drawings in which.

DETAILED DESCRIPTION

Figure 1A:
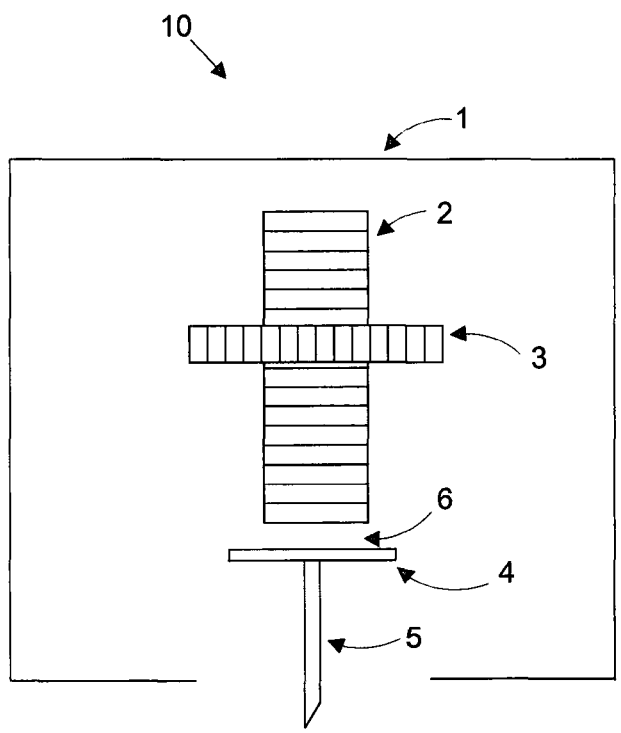
FIG. 1A shows a cross-section schematic of a needle delivery device according to a first embodiment of the invention in a first rest position.

A needle delivery device according to a first embodiment of the invention is shown in FIGS. 1A to 3 and is designated generally by reference numeral 10.

FIG. 1A is a cross-section schematic of the needle delivery device 10 shown in a first rest position. The needle delivery device 10 includes a device housing 1 which contains a drive mechanism. The drive mechanism includes a threaded drive member 2 and a fixed drive plate 3.

The drive member 2 moves linearly relative to the fixed drive plate 3 upon rotation of the drive member 2. Thus, the drive member 2 and the fixed drive plate 3 act as a screw-thread drive mechanism.

The housing 1 also contains a contact member 6 which defines a contact region between the drive mechanism, in particular the drive member 2, and a needle assembly. The needle assembly includes a needle base plate 4 and a needle 5.

Figure 1B:
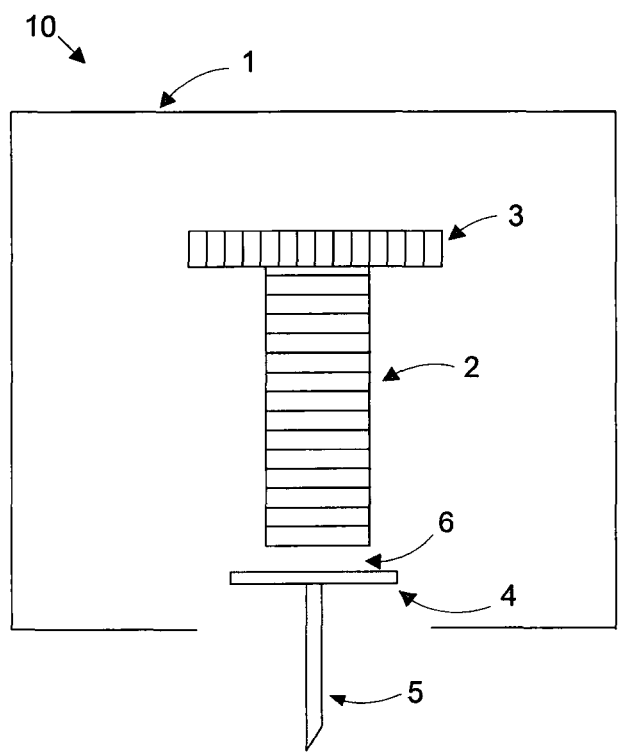
FIG. 1B shows a cross-section schematic of the needle delivery device of FIG. 1A in a second activated position.

FIG. 1B shows a cross-section schematic of FIG. 1A in a second activated position whereby it is noticed that the fixed drive plate 3 has not moved, but the drive member 2 has moved relative to the fixed drive plate 3. The needle 5 is now in an activated position whereby it has left the device housing 1 and penetrated the skin (skin not shown).

It will be apparent that the needle orientation has not changed in that despite using a screw-thread drive mechanism the needle orientation is kept fixed, and the mechanism acts to exert a force on the needle 5 to drive it in to the skin rather than causing it to rotate. This is critical to minimise the trauma to the skin since the needle 5 may not be concentric, nor may any solid dose attached to the needle 5, and therefore if the entire needle 5 was to rotate then this would lead to increased trauma to the skin.

The surface of the contact member 6 between the needle base plate 4 and the drive member 2 is a low friction surface produced from metal, plastic or glass or other suitable material, or a combination thereof.

Figure 2:
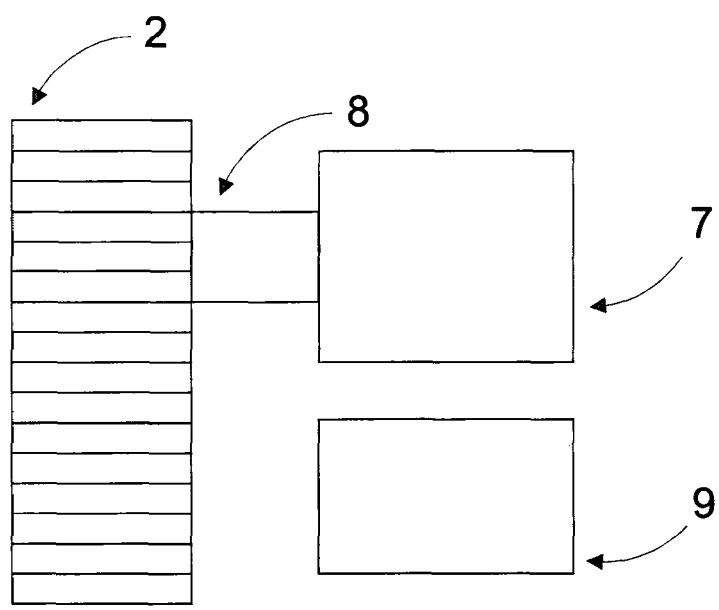
FIG. 2 shows a schematic of a portion of the drive mechanism of the needle delivery device shown in FIG. 1A.

FIG. 2 is a plan view of the drive member 2, a feedback control box 7 which is linked by a control loop interface 8, and a power supply 9. The feedback control loop box 7 houses electronic circuitry and a suitable actuator such as a linear drive motor or a normal motor/gear arrangement designed to drive the drive member 2.

The feedback control loop box 7 will also receive feedback in terms of the puncture force thus it is able to determine when the needle has pierced through the skin, and thus when the drive speed can be ramped up for rapid insertion in to the skin (the force gauge is not shown as it may be a simple digital sensor built into a printed circuit board of the control box 7, with suitable software control). Similarly the control box 7 can provide a pre-programmed sequence for the injection of the drug in to the skin at different depths.

Figure 3:
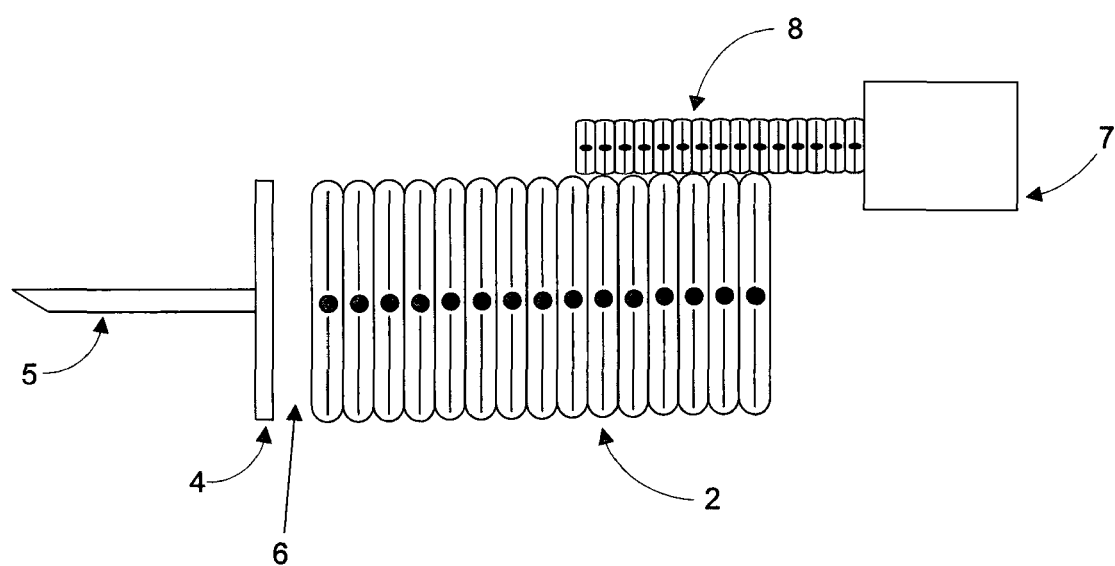
FIG. 3 shows a cross-section of a portion of the needle delivery device shown in FIG. 1A together with a portion of the drive mechanism shown in FIG. 2.

FIG. 3 is a cross-section of the drive member 2 relative to the control loop interface 8 and control box 7. The function of the control loop interface 8 in this case is not only to convey data on the resistive force back to the control box 7 but also to act as a drive mechanism to drive the drive member 2.

It will be appreciated that whilst a screw-thread drive mechanism has been shown in the illustrations, there may be other suitable drive mechanisms established in the current state of the art that would be equally suitable.

Figure 4:
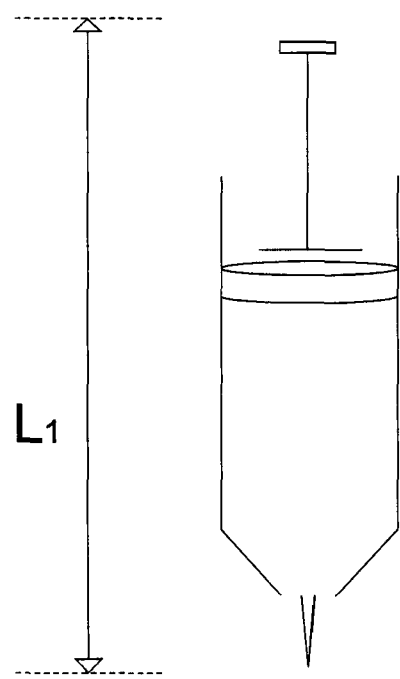
FIG. 4 shows a conventional plunger arrangement being used in a syringe.

FIG. 4 shows a conventional plunger rod in the extended position. When you take in to account the full extended position and the outer housing, the length of the device can no longer fit in to the palm, and is quite cumbersome.

A plunger mechanism according to a second embodiment of the invention is shown in FIGS. 5 to 8 and is designated generally by reference numeral 20.

Figure 5:
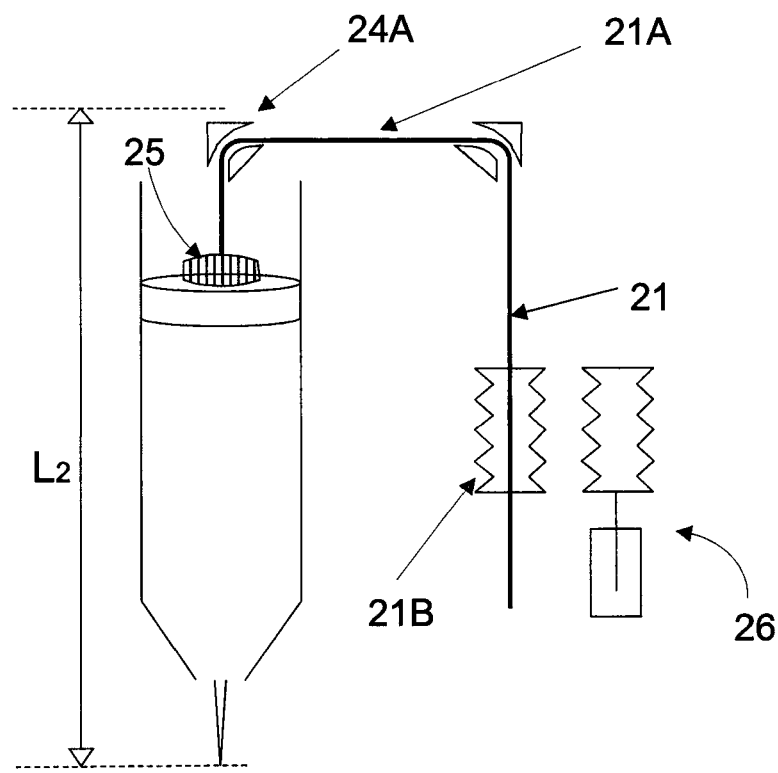
FIG. 5 shows a schematic of a plunger mechanism according to second embodiment of the invention.

FIG. 5 shows the plunger mechanism 20 which includes a plunger rod 21 that has first and second opposed ends and a flexible portion 21A extending therebetween. The flexible portion 21A may be made from a malleable material, such as a polymer or a thinned extrusion of metal. The flexible portion 21A may be formed from any suitable material which permits it to bend around an arch. The material may also have high rigidity when it is in the straight position. The flexible portion 21A may be formed from the same or different material to the remainder of the plunger rod 21.

In the embodiment shown the first end includes a disc 25 which is abuttable in use to a stopper of a syringe. In particular, the stopper is moveable within a barrel of a syringe so as to push a drug dose contained within the barrel out of one end of the barrel. The first end may take any form which enables it to push the stopper (or septum constructed of a suitable material such as rubber, Teflon, or other polymeric or glass composition) in a pre-filled vial or barrel.

The second end of the plunger rod 21 includes a threaded portion 21B. The plunger mechanism 20 further includes an actuator 26 which is threadably engaged with the threaded portion 21B of the plunger rod 21, wherein rotational movement of the actuator 26 drives the plunger rod 21 linearly along the length of the threaded portion 21B.

Figure 6:
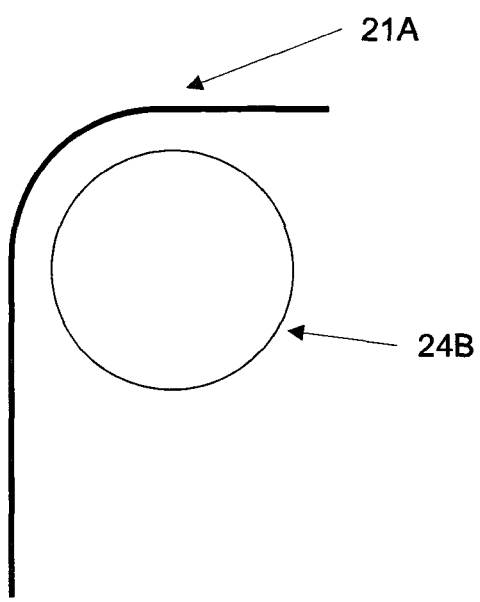
FIG. 6 shows a schematic of a portion of the plunger mechanism shown in FIG. 5.

The flexible portion 21A of the plunger rod 21 is bent around a guide slot 24A, as shown in FIG. 5. The plunger rod 21 may instead be bent around a pulley system which includes a wheel 24B over which the flexible portion 21A of the plunger rod 21 is bent, as shown in FIG. 6. In both instances, since the first and second ends of the plunger rod 21 are positioned parallel with one another and in close proximity to one another, the device is now compact and at least 30% shorter than the conventional device shown in FIG. 4.

Figure 7A:
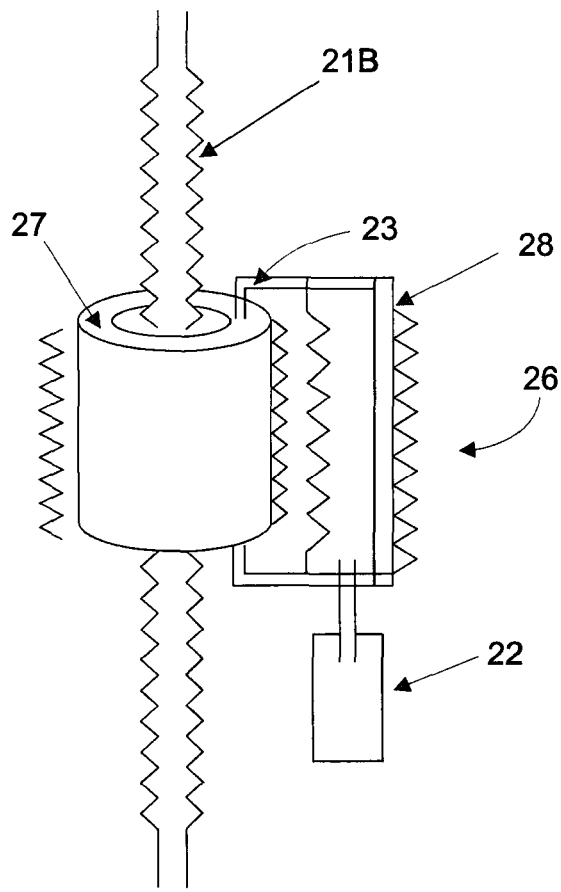
FIG. 7A shows a schematic of one arrangement of an actuator of the plunger mechanism.

FIG. 7A shows one arrangement of the actuator 26. In this arrangement, the actuator 26 includes a screw thread nut 27 which shrouds the threaded portion 21B of the plunger rod 21, and a threaded member 28 positioned adjacent to and threadably engaged with the screw thread nut 27.

The FIG. 7A arrangement also includes arms 23 that keeps the screw thread nut 27 in a restrained position so that the threaded portion 21B of the plunger rod 21 can move relative to the screw thread nut 27 when it is rotated.

Figure 7B:
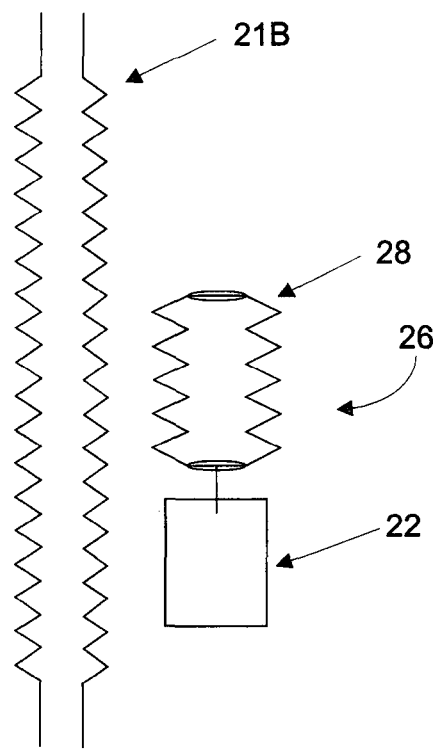
FIG. 7B shows a schematic of another arrangement of an actuator of the plunger mechanism.

FIG. 7B shows an alternative arrangement of the actuator 26. In this arrangement, the actuator 26 omits the screw thread nut. Instead, the threaded portion 21B of the plunger rod 21 is threadably engaged directly with the threaded member 28.

In both the FIG. 7A and FIG. 7B arrangements, the threaded member 28 is driven by a motor 22 which rotates the threaded member 28.

Figure 8:
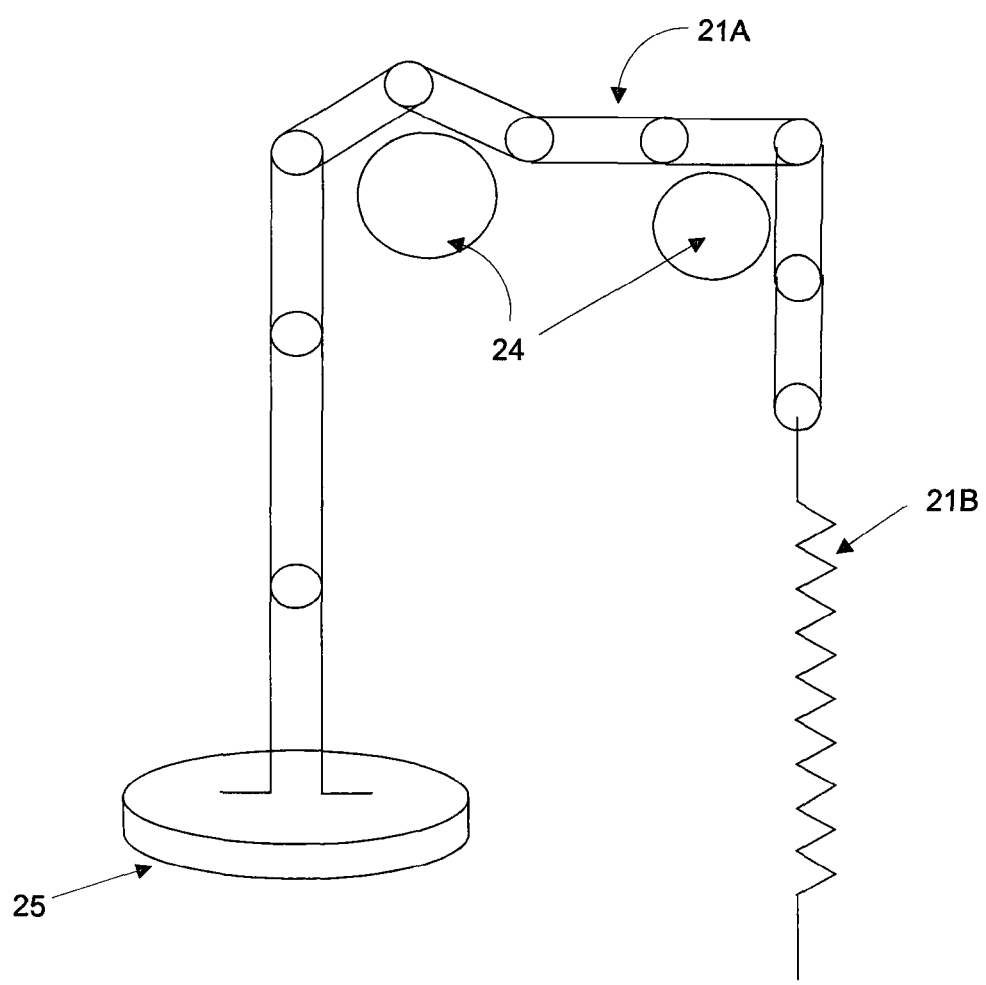
FIG. 8 shows a schematic of an alternative embodiment of the plunger mechanism.

FIG. 8 shows an alternative embodiment of the plunger mechanism. The alternative embodiment shares features of the embodiment described hereinabove and like features have the same reference numerals. The actuator is not shown but it could take the form of either of the arrangements shown in FIGS. 7A and 7B.

In the alternative embodiment, the flexible portion 21A of the plunger rod 21 is made from inter-linked parts which enables the plunger rod 21 to travel around an arch, i.e. provides its flexibility.

Figure 9:
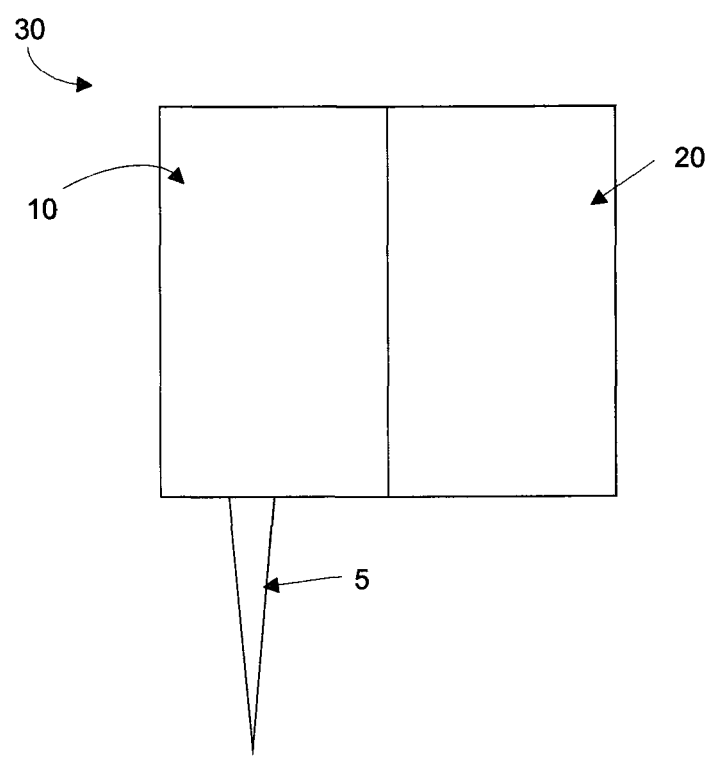
FIG. 9 shows a schematic of a syringe according to a third embodiment of the invention.

A syringe according to a third embodiment of the invention is shown in FIG. 9 and is designated generally by reference numeral 30.

The syringe 30 includes a needle delivery device 10 as described hereinabove and shown in FIGS. 1 to 3 and a plunger mechanism 20 as described hereinabove and shown in FIGS. 5 to 8.

The needle delivery device 10 and the plunger mechanism 30 are operatively coupled to another so that the needle delivery device 10 can deploy the needle 5, thus penetrating skin or a patient, and the plunger mechanism 20 can deliver a dose of drugs at a predetermined depth.

In particular, the control assembly of the needle delivery device 10 is synchronised with the plunger mechanism 20. The programmable electronic controller, i.e. the control box 7, of the control assembly can be pre-programmed to control the drive mechanism to drive the drive member 2 to a first pre-determined depth, followed by control of the plunger mechanism 20 to deliver a pre-determined volume of drug. This can be repeated at different depths of the skin.

The invention claimed is:

1. A needle delivery device comprising:
   a needle assembly;
   a drive mechanism including a drive member, the drive member being linearly moveable upon rotation of the drive member; and
   a contact member positioned between and abutting the needle assembly and the drive member, the contact member being configured to provide only linear motion to the needle assembly upon rotation of the drive member so as to drive movement of the needle assembly between a distal and proximal position relative to the needle delivery device.

2. The needle delivery device according to claim 1 wherein a surface of the contact member abutting the drive member provides a low friction which prevents translation of the rotational movement of the drive member to the contact member.

3. The needle delivery device according to claim 2 wherein the low friction is provided by a low friction material.

4. The needle delivery device according to claim 1 wherein the drive member includes a threaded shaft and the drive mechanism further includes a fixed drive plate, wherein the threaded shaft and the fixed drive plate are threadably engaged with one another.

5. The needle delivery device according to claim 1 further including a control assembly operatively coupled to the drive mechanism and being configured to provide a rotational drive to the drive mechanism at variable driving speeds.

6. The needle delivery device according to claim 5 wherein the control assembly is configured to increase the driving speed once the needle assembly has penetrated the skin.

7. The needle delivery device according to claim 6 wherein the needle delivery device further comprises a sensor and wherein the control assembly receives data from the sensor which is configured to detect when the needle assembly has penetrated the skin.

8. The needle delivery device according to claim 5 wherein the control assembly is also operatively coupled to a plunger mechanism of the needle delivery device, the control assembly being further configured to activate the plunger mechanism so as to expel a liquid pharmaceutical composition at a predetermined distance of linear movement of the drive member.

9. The needle delivery device according to claim 8 wherein the control assembly is further still configured to activate the plunger mechanism at a number of discrete predetermined distances of linear movement of the drive member so as to expel a desired volume of pharmaceutical composition at each discrete predetermined distance.

10. The needle delivery device according to claim 9 wherein a first discrete predetermined distance is at a proximal position relative to the needle delivery device and the last discrete predetermined distance is at a distal position relative to the needle delivery device.

11. The needle delivery device according to claim 5 wherein the control assembly provides the rotational drive to the drive member.

12. The needle delivery device according to claim 5 wherein the control assembly includes a motor which provides the rotational drive.

13. The needle delivery device according to claim 5 wherein the control assembly includes an electronic controller which is pre-programmable.

14. A plunger mechanism for a drug injection device, comprising a needle delivery device comprising a needle assembly, a drive mechanism including a drive member, the drive member being linearly moveable upon rotation of the drive member, and a contact member positioned between and abutting the needle assembly and the drive member, the contact member being configured to provide only linear motion to the needle assembly upon rotation of the drive member so as to drive movement of the needle assembly between a distal and proximal position relative to the needle delivery device; and
   a plunger rod having first and second opposed ends and a flexible portion extending therebetween, the first end being abuttable in use to a stopper and the second end including a tractive portion, the plunger mechanism further including an actuator in contact with the tractive portion of the plunger rod, wherein movement of the actuator drives the plunger rod linearly along the length of the tractive portion.

15. The plunger mechanism according to claim 14 wherein the first and second ends of the plunger align parallel with one another with the flexible portion being bent therebetween.

16. The plunger mechanism according to claim 14 wherein the tractive portion of the plunger rod is threaded.

17. The plunger mechanism according to claim 16 wherein the actuator includes a threaded member positioned adjacent to and threadably engaged with the threaded portion of the plunger rod.

18. The plunger mechanism according to claim 17 wherein the actuator includes a threaded nut surrounding the threaded portion of the plunger rod and a threaded member positioned adjacent to and threadably engaged with the threaded nut.

19. A syringe comprising:
   a needle delivery device comprising:
      a needle assembly;
      a drive mechanism including a drive member, the drive member being linearly moveable upon rotation of the drive member; and a contact member positioned between and abutting the needle assembly and the drive member, the contact member being configured to provide only linear motion to the needle assembly upon rotation of the drive member so as to drive movement of the needle assembly between a distal and proximal position relative to the needle delivery device; and a plunger mechanism comprising a plunger rod having first and second opposed ends and a flexible portion extending therebetween, the first end being abuttable in use to a stopper and the second end including a tractive portion, the plunger mechanism further including an actuator in contact with the tractive portion of the plunger rod, wherein movement of the actuator drives the plunger rod linearly along the length of the tractive portion.

20. The syringe according to claim 19 wherein the needle delivery device and the plunger mechanism are operatively coupled to one another.

\* \* \* \* \*